United States Patent [19]

Fischell et al.

[11] Patent Number: 5,830,227
[45] Date of Patent: Nov. 3, 1998

[54] BALLOON ANGIOPLASTY CATHETER WITH ENHANCED CAPABILITY TO PENETRATE A TIGHT ARTERIAL STENOSIS

[75] Inventors: Robert E. Fischell, Dayton, Md.;
David R. Fischell, Fair Haven, N.J.;
Tim A. Fischell, Richland, Mich.

[73] Assignee: IsoStent, Inc., Belmont, Calif.

[21] Appl. No.: 840,788

[22] Filed: Apr. 16, 1997

[51] Int. Cl.⁶ .................................................. A61M 29/00
[52] U.S. Cl. .............................................. 606/194; 604/96
[58] Field of Search ..................... 604/96, 102; 606/108, 606/192, 194

[56] References Cited

U.S. PATENT DOCUMENTS

| | | | |
|---|---|---|---|
| 5,295,961 | 3/1994 | Niederhauser et al. | 604/96 |
| 5,395,332 | 3/1995 | Ressemann et al. | 604/96 |
| 5,653,689 | 8/1997 | Buena et al. | 604/96 |

Primary Examiner—Corrine M. McDermott

[57] ABSTRACT

The present invention is a balloon angioplasty catheter that combines a catheter shaft having increased pushability with an elongated, gradually tapered, highly flexible, lubricity coated, distal tip that is specifically designed to penetrate through a tight stenosis. The distal end of the tip is formed as a very thin-walled, tapered, frustrum of a cone that is capable of following a guide wire through even the most tortuous coronary arteries. The proximal end of the tip has a diameter that is equal to or slightly larger than the diameter of an angioplasty balloon that is wrapped around a catheter shaft at a distal section of the balloon angioplasty catheter. One embodiment of the invention includes a thin-walled tube located at the proximal end of the distal tip which extends over the distal end of the angioplasty balloon. This design can prevent the distal end of the wrapped pre-deployed balloon from engaging the arterial wall as it is pushed through a tight stenosis. The balloon angioplasty catheter can be designed with the capability for either or both a rapid exchange or over-the-wire mode.

7 Claims, 4 Drawing Sheets

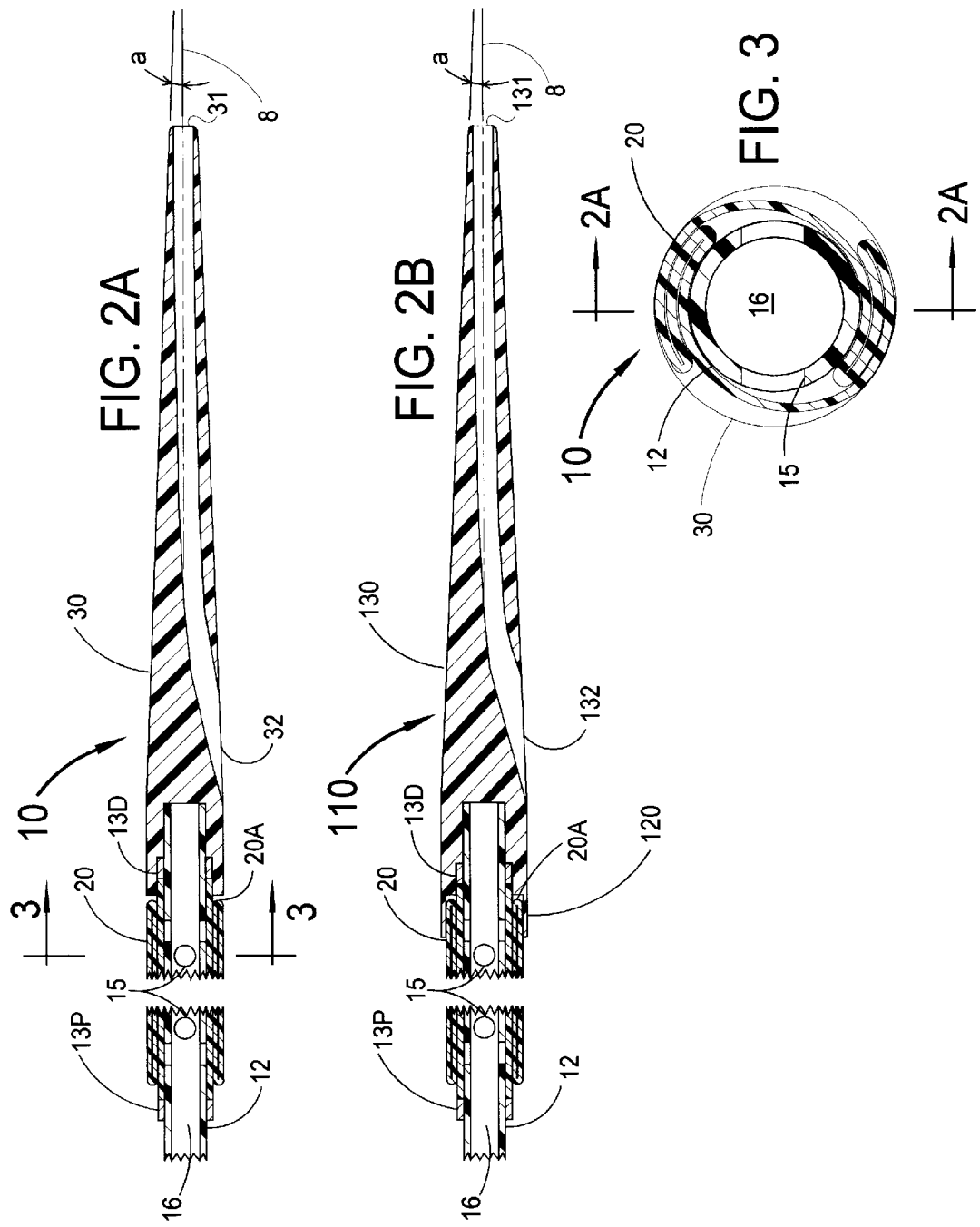

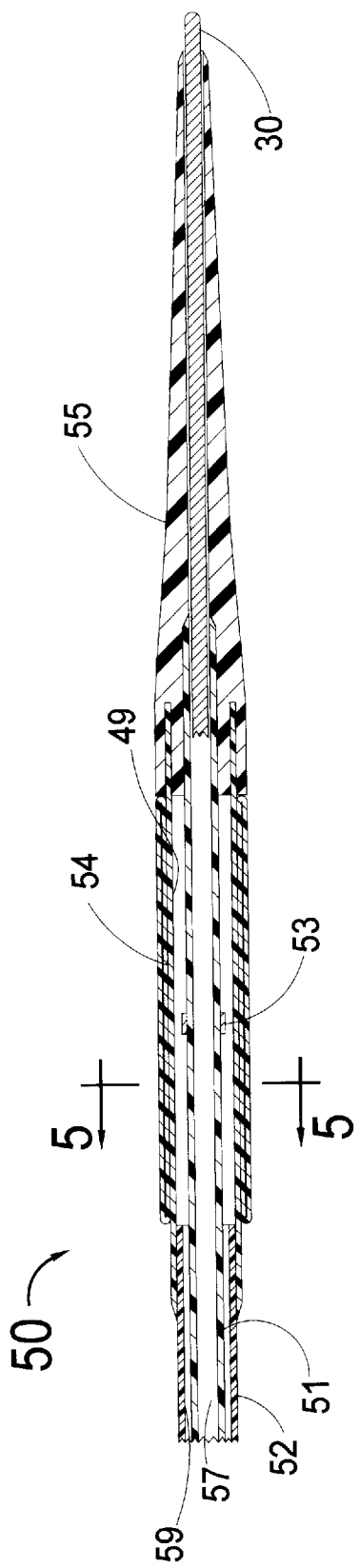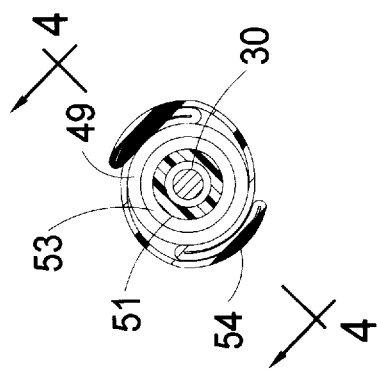
FIG. 4
FIG. 5

2

BALLOON ANGIOPLASTY CATHETER WITH ENHANCED CAPABILITY TO PENETRATE A TIGHT ARTERIAL STENOSIS

THE FIELD OF USE

This invention is a balloon angioplasty catheter that is used for dilatation of stenotic arteries in human subjects.

BACKGROUND OF THE INVENTION

A very important attribute for a balloon angioplasty catheter is to penetrate through a tight arterial stenosis. By a tight stenosis is meant a narrowing in an artery where the minimal luminal diameter is less than approximately 0.7 mm. Such "tight stenoses" would include a total blockages of the artery.

The well known attribute for a balloon angioplasty catheter to allow passage through such a tight stenosis is low profile; i.e., a small outside diameter at the distal section of the balloon angioplasty catheter. However, low profile has the disadvantage of disallowing balloons that are thick walled which are desirable for high pressure dilatation of a hard stenosis. Furthermore, any balloon angioplasty catheter that requires a guide wire to pass through an inner shaft as well as through the balloon of the balloon angioplasty catheter results in an increased profile at the distal section of the catheter.

Still further, prior art balloon angioplasty catheters have a distal section that does not have a truly gradual taper. Therefore, they create more resistance to being pushed through a tight stenosis as compared to a structure that has a gradually tapered distal tip.

SUMMARY OF THE INVENTION

The present invention is a balloon angioplasty catheter that combines a catheter shaft having increased pushability with an elongated, gradually tapered, highly flexible, lubricity coated, distal tip that is specifically designed to penetrate through a tight stenosis. The distal end of the tip is formed as a very thin-walled, tapered, frustrum of a cone that is capable of following a guide wire through even the most tortuous coronary arteries. The proximal end of the tip has a diameter that is equal to or slightly larger than the diameter of an angioplasty balloon that is wrapped around a catheter shaft at a distal section of the balloon angioplasty catheter. One embodiment of the invention includes a thin-walled tube located at the proximal end of the distal tip which extends over the distal end of the angioplasty balloon. This design can prevent the distal end of the wrapped uninflated balloon from engaging the arterial wall as it is pushed through a tight stenosis.

The balloon angioplasty catheter can have one or two elongated, coaxial cylindrical shafts that extend from the balloon angioplasty catheter's proximal end to the proximal end of the distal tip. By employing a woven metal wire elongated tubular structure onto which a plastic material is extruded, the shaft(s) of the balloon angioplasty catheter can provide increased pushability even though such a catheter employing metal wire would be somewhat less flexible as compared to a typical extruded plastic balloon angioplasty catheter shaft that does not include any metal wire. However, because of the comparatively long and extremely gradual taper of the balloon angioplasty catheter's distal tip, penetration of even a very tight stenosis becomes practical. In fact, an elongated, conically tapered, distal tip can provide stenotic dilatation (called "Dottering") of a tight stenosis when the shaft(s) of the balloon angioplasty catheter apply a distally directed force at the proximal end of the distal tip to push the distal tip through a tight stenosis. The larger diameter at the proximal end of the tip can dilate the stenosis sufficiently so that a multi-fold balloon located just proximal to the tip's proximal end can be easily passed through such a dilated stenosis. It should be noted that the outside diameter of the non-deployed balloon is equal to or slightly smaller than the diameter of the tip at the tip's proximal end.

In one embodiment of this invention, the tip can have a central lumen throughout its length which would be the design for an "over-the-wire" type of balloon angioplasty catheter which is characterized by having the guide wire exit ports located at the proximal end and the distal end of the balloon angioplasty catheter. Another embodiment of this invention can have the guide wire distal exit port located at the distal end of the balloon angioplasty catheter, but the guide wire's proximal exit port would be placed at the side of the gradually tapered distal tip near the tip's proximal end and distal to the balloon. Such a balloon angioplasty catheter design is said to have a "rapid exchange" capability.

Still another embodiment of the invention utilizes both a lumen placed through the distal tip and a second lumen that has the same distal exit port but has a guide wire proximal exit port located at the side of the distal tip near the tip's proximal end. Thus, this balloon angioplasty catheter would provide either over-the-wire or rapid exchange capability depending on how the guide wire was threaded through the distal tip.

A most important aspect of this invention is that the balloon angioplasty catheter's distal tip is an elongated frustrum of a cone having an extraordinarily gradual taper as opposed to prior art designs where the distal section of the balloon angioplasty catheter has several portions each of which is a short, steeply tapered portion or a short cylindrical portion having no taper what-so-ever. Any portion of a balloon angioplasty catheter's distal section that has a comparatively steep slope angle increases the distally directed push force required to push that balloon angioplasty catheter's distal section through a tight stenosis as compared to the force required to push through a gradually tapered distal tip that has an extraordinarily small slope angle throughout its entire length.

Thus, one object of this invention is to have a balloon angioplasty catheter with increased distally directed pushability combined with an elongated, gradually tapered, distal tip with a continuous outer surface having a slope angle of less than 3 degrees thus providing a system for penetration of a tight stenosis by Dottering.

Another object of this invention is to have a balloon angioplasty catheter with a continuously tapered distal tip that requires less push force to penetrate through a tight stenosis as compared to a distal section of a balloon angioplasty catheter that has a few portions that have a steep slope angle and others that are cylindrical portions that have a zero slope angle.

Still another object of this invention is to have the gradually tapered distal tip utilize a central through lumen to provide an over-the-wire balloon angioplasty catheter design.

Still another object of this invention is to have a gradually tapered distal tip that has a guide wire proximal exit port at the side of the distal tip near the distal tip's proximal end and a guide wire distal exit port at the tip's distal end thus providing a rapid exchange capability for the balloon angioplasty catheter.

Still another object of this invention is to have a gradually tapered distal tip for the balloon angioplasty catheter that has both a central lumen and a guide wire proximal exit port at the side of the distal tip near its proximal end thus providing either over-the-wire or rapid exchange capability for the balloon angioplasty catheter.

Still another object of this invention is to have a gradually tapered distal tip that provides predilatation of a tight stenosis by Dottering prior to inflating the balloon of the balloon angioplasty catheter which balloon provides additional dilatation after the balloon is inflated.

Still another object of this invention is to use a single shaft for the balloon angioplasty catheter without a guide wire placed within that shaft, the interior passageway of the shaft being the inflation lumen for the balloon, the single shaft allowing a smaller outside diameter for the wrapped, uninflated balloon thus allowing a smaller diameter (i.e., lower profile) for the distal section of the balloon angioplasty catheter.

These and other important objects and advantages of this invention will become apparent from the detailed description of the invention and the associated drawings provided herein.

BRIEF DESCRIPTION OF THE DRAWINGS

FIG. 2A is a longitudinal cross section of a distal section of a first embodiment of a balloon angioplasty catheter having a gradually tapered distal tip with a guide wire proximal exit port located near the proximal end of the distal tip for providing rapid exchange capability.

FIG. 2B is a longitudinal cross section of a distal section of a second embodiment of a balloon angioplasty catheter having a gradually tapered distal tip with a guide wire proximal exit port located near the proximal end of the distal tip for providing rapid exchange capability; the distal tip also having a thin-walled cylinder at it proximal end that extends over the distal end of the uninflated balloon.

FIG. 3 is a transverse cross section of the rapid exchange balloon angioplasty catheter at section 3—3 of FIG. 2A.

FIG. 4 is longitudinal cross section of another embodiment of a distal section of a balloon angioplasty catheter with a gradually tapered distal tip.

FIG. 5 is a transverse cross section of the balloon angioplasty catheter at section 5—5 of FIG. 4.

FIG. 7 is a longitudinal cross section at section 7—7 of FIG. 5 of the embodiment of the invention shown in FIGS. 4 and 5.

DETAILED DESCRIPTION OF THE INVENTION

Figure 1:
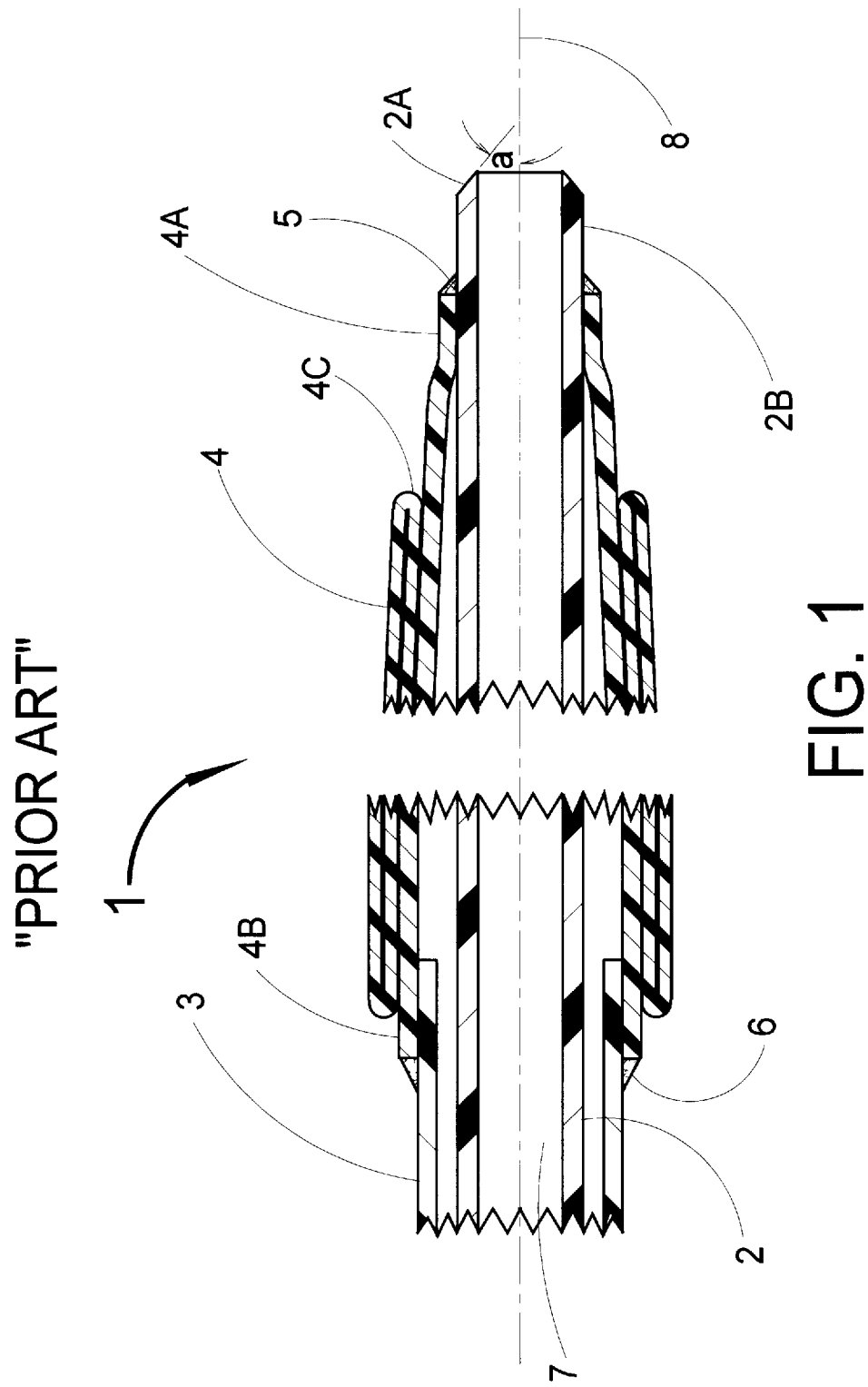
FIG. 1 is a longitudinal cross section of a distal section of a conventional, prior art balloon angioplasty catheter.

FIG. 1 illustrates the distal section of a conventional, prior art, balloon angioplasty catheter 1 having an inner shaft 2, an outer shaft 3, an inflatable balloon 4, adhesive joints 5 and 6, central lumen 7 and a longitudinal axis 8. The inner shaft 2 has a somewhat steeply tapered distal portion 2A that makes a slope angle "a" with the longitudinal axis 8. This slope angle "a" is typically greater than 20 degrees and always greater than 5 degrees. Just proximal to the distal portion 2A is a cylindrical portion 2B that has a zero slope angle.

At the distal and proximal ends of the balloon 4, some balloon angioplasty catheters use a thin wedge of adhesive to join the balloon 4 at its distal end to the inner shaft 2 and at the balloon's proximal end to the distal end of the outer shaft 3. Thus the adhesive wedge portions 5 and 6 each have a taper which typically might have a slope angle that is greater than 10 degrees.

The balloon 4 has a distal cylindrical portion 4A that is fixed to the inner shaft 2 and a proximal cylindrical portion 4B that is joined to the distal end of the outer shaft 3. Both cylindrical portions 4A and 4B have a zero slope angle. The balloon 4 has a comparatively blunt distal fold 4C which can be difficult to push through a tight arterial stenosis. To ease the insertion of such a balloon 4 through a tight stenosis, manufacturers of balloon angioplasty catheter 5 always strive for a "low profile" distal section of their balloon angioplasty catheter. "Low profile" really means as small an outside diameter as possible so that the blunt distal fold 4C of the balloon 4 would not prevent passage of the distal section of the balloon angioplasty catheter through a tight stenosis. This requirement for the ultimate in low profile, typically dictates inflatable balloons with a very thin wall thus limiting the burst pressure of the balloon thus limiting the capability of the balloon to dilate a hard (calcified) stenosis.

The balloon angioplasty catheters 10 and 110 as shown in FIGS. 2A, 2B and 3 are designed to overcome many of the shortcomings of the prior art balloon angioplasty catheters. Specifically, the balloon angioplasty catheters 10 and 110 each utilize a gradually tapered distal tip (30 and 130 respectively) in the form of a frustrum of a cone, the cone having an extraordinarily gradual taper in order to penetrate even the tightest stenosis even when using, high pressure balloons that do not have a very low profile; i.e., that have a comparatively large outside diameter. However, because there is no portion of the distal section of the balloon angioplasty catheter 10 that has either a steep slope angle or a wrapped balloon with a blunt distal fold that can catch on a tight stenosis, the balloon angioplasty catheters 10 and 110 can more readily penetrate through even a very tight stenosis.

The balloon angioplasty catheters 10 and 110 shown in FIGS. 2A, 2B and 3 each has a single elongated cylindrical shaft 12 with a balloon inflation lumen 16 through which inflation fluid can be used to inflate or deflate the balloon 20 by means of the side hole 15. A proximal radiopaque marker band 13P and a distal radiopaque marker band 13D are used to indicate by fluoroscopy that the balloon 20 is centered within an arterial stenosis. The balloon angioplasty catheters 10 and 110 each has an elongated, gradually, tapered distal tip 30 or 130 whose outer surface makes a slope angle "a" with the longitudinal axis 8 of the distal tip 30. By "gradually tapered" is meant an average slope angle "a" over the length of the distal tip 30 or 130 that is typically less than 1.0 degree and always less than 3 degrees. The length of the distal tip 30 typically lies between 1 and 5 cm.

The balloon angioplasty catheter 110 shown in FIG. 2B has a thin-walled cylindrical section 120 that extends from the proximal end of the distal tip 130 over the blunt distal fold 20A of the balloon 20. This design guarantees that the blunt distal fold 20A of the balloon 20 will not engage the wall of a tight stenosis which could prevent the passage of the distal section of the balloon angioplasty catheter 110 from penetrating such a tight stenosis.

Either the distal tip 30 or 130 of the balloon angioplasty catheter 10 or 110 as shown in FIGS. 2A and 2B is capable of Dottering through a tight stenosis because of the absence of any distal portions of the balloon angioplasty catheter 10 or 110 that have either a steep slope angle or a wrapped balloon with a blunt distal fold. By "Dottering" is meant pushing a tapered distal tip of a catheter through a stenosis thereby achieving dilatation of that stenosis. When the distal tip 30 or 130 of the balloon angioplasty catheter 10 or 110 would be pushed through a stenosis, it would perform a pre-dilatation function. Final dilatation of the stenosis would be achieved by inflating the balloon 20 to a high pressure, typically greater than 15 atmospheres. Because the distal tip 30 or 130 pre-dilates the stenosis, the profile or outside diameter of the balloon 20 can be increased thus allowing a thicker balloon wall thus providing the desired high balloon inflation pressure capability.

FIGS. 2A and 2B show that the distal tip 30 or 130 has a guide wire distal exit port 31 or 131 and a guide wire proximal exit port 32 or 132. For the sake of clarity, no guide wire is shown in either FIG. 2A, 2B or FIG. 3. The presence of proximal exit port 32 or 132 for entry and exiting of a guide wire determines that the balloon angioplasty catheter 10 or 110 shown in FIGS. 2A and 2B each has rapid exchange capability.

Since no guide wire is required to pass through the central lumen 16 of the shaft 12, the outsider diameter of the shaft 12 can be smaller that the outside diameter of the inner shaft for any conventional balloon angioplasty catheter through which a guide wire is placed such as the balloon angioplasty catheter 1 shown in FIG. 1. This reduced outside diameter for the shaft 12 allows a smaller outside diameter for the wrapped balloon 20 as compared to a larger, outside diameter required for the prior art balloon 4 of the balloon angioplasty catheter 1 shown in FIG. 1.

Although the shaft 12 can be made entirely from a plastic material, improved pushability for the balloon angioplasty catheter 10 can be obtained by making the shaft 12 from a thin-walled metal tube or an elongated woven wire cylinder over which a flexible plastic is extruded. Such tubular structures are well known in the art of extruding tubing for intravascular catheters. Furthermore, to improve pushability through a tight stenosis, the distal tip (as seen in FIGS. 2A, 2B, 4, 6A and 6B) should have a shape which is the frustrum of a cone having its smallest diameter at the distal end of the distal tip. Preferably the tip should be conical in shape starting at the tip's distal end and extending for at least 50% of the tip's length.

FIGS. 4 and 5 illustrate an alternative embodiment of the invention which is a balloon angioplasty catheter 50 having an inner shaft 51, an outer shaft 52, a radiopaque marker band 53, an inflatable balloon 54 and a distal tip 55. The annular passageway 59 is in fluid communication with the interior chamber 49 of the balloon 54. Thus, the passageway 59 is used for inflation and deflation of the balloon 54. A guide wire 30 can be moved slideably through the central lumen 57 that extends through the entire length of the balloon angioplasty catheter 50 to achieve an over-the-wire mode. If the guide wire 30 has a guide wire proximal exit port that is within approximately 5 to 25 cm. proximal to the balloon 54, then a rapid exchange mode is achieved.

Figure 6A:
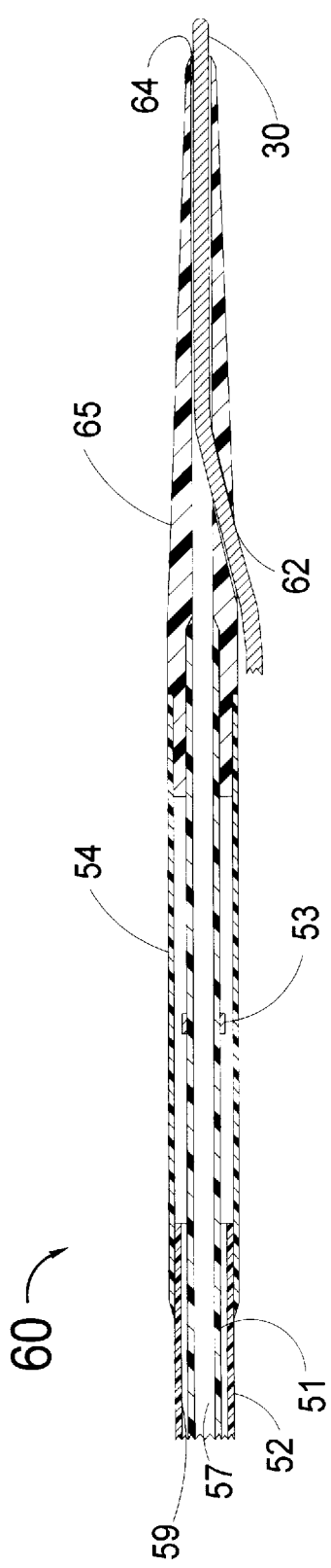
FIG. 6A is a longitudinal cross section of a distal section of a balloon angioplasty catheter that provides either over-the-wire or a rapid exchange capability with a guide wire shown for the balloon angioplasty catheter being used in its rapid exchange mode.
Figure 6B:
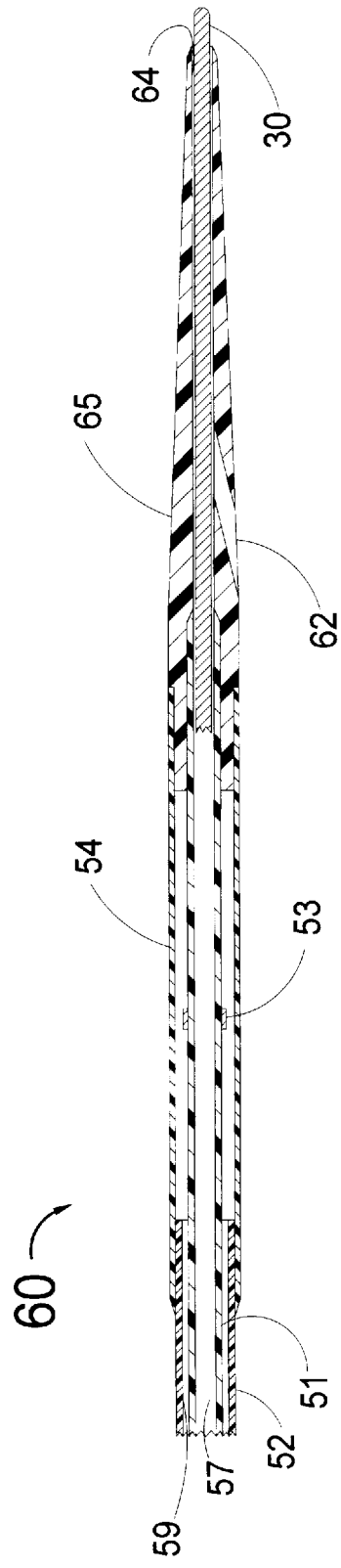
FIG. 6B is a longitudinal cross section of a distal section of a balloon angioplasty catheter that provides either over-the-wire or a rapid exchange capability with a guide wire shown for the balloon angioplasty catheter being used in over-the-wire mode.

FIGS. 6A and 6B illustrate a balloon angioplasty catheter 60 that can provide either over-the-wire or rapid exchange capability. Specifically, this design has an inner shaft 51, outer shaft 52, radiopaque marker band 53, balloon 54, and a distal tip 65 which has a guide wire proximal exit port 62 and guide wire distal exit port 64. As seen in FIG. 6A, when the guide wire 30 exits the distal tip 65 at the guide wire's proximal exit port 62, one achieves a rapid exchange mode. As seen in FIG. 6B, when the guide wire 30 exits at the proximal end (not shown) of the balloon angioplasty catheter 60 that lies outside the patient's body, then an over-the-wire mode is achieved. Therefore, the balloon angioplasty catheter 60 can be used in either an over-the-wire or rapid exchange mode depending on which guide wire proximal exit port is used.

It should be noted that the gradually tapered distal tips 30, 130, 55 and 65 of FIGS. 2A, 2B, 4, 6A and 6B have a common feature which is an important aspect of this invention, namely a gradually tapered shape which is a frustrum of a cone that has a continuous outer surface. "Continuous outer surface" is defined herein as one that does not have abrupt changes in slope as noted for the distal section of the prior art balloon angioplasty catheter 1 illustrated in FIG. 1. Such a continuous outer surface allows a decreased force to push it through a tight stenosis as compared to the distal section of a conventional, prior art balloon angioplasty catheter. The conventional prior art balloon angioplasty catheter has a distal portion that has a sloped angle greater than 10 degrees followed by a centrally located cylindrical portion which has a zero slope angle. Although a continuous outer surface may have a proximal or a distal portion that has a zero slope angle, the distal tip's central portion is characterized by a non-zero slope that is always less than 3 degrees and optimally less than 1 degree.

It should be noted that, for the sake of clarity, FIGS. 1, 2A, 2B, 4, 6A and 6B each exaggerates transverse dimensions as compared to longitudinal dimensions. Thus the balloon angioplasty catheters 10, 110, 50 and 60 would optimally be much thinner and longer as to compared to what is shown in these FIGS.

Various other modifications, adaptations, and alternative designs are of course possible in light of the above teachings. Therefore, it should be understood at this time that within the scope of the appended claims, the invention may be practiced otherwise than as specifically described herein.

What is claimed is:

1. A balloon angioplasty catheter system for the dilation of an arterial stenosis in a human subject, the balloon angioplasty catheter system comprising:

a flexible guide wire, a balloon angioplasty catheter having a single elongated hollow cylindrical shaft which has a single lumen, the shaft having a proximal end and a distal end, the shaft extending for most of the length of the balloon angioplasty catheter, the balloon angioplasty catheter having a proximal end that is placed outside of the body of the human subject and having a distal section at which distal section an uninflated balloon is fixedly attached to the shaft, the balloon having a proximal end and a distal end and having a blunt distal fold located just proximal to the balloon's distal end; and an elongated gradually tapered distal tip in the general form of a frustrum of a cone having a continuous outer surface, the frustrum of the cone extending throughout the distal end of the balloon angioplasty catheter, the cone having its smallest diameter at the distal end of the distal tip, the distal tip having a proximal end that is situated immediately adjacent to the blunt distal fold of the uninflated balloon, the tip also being directly and fixedly attached to the distal end of the uninflated balloon, and the distal tip also having a distal end and a guide wire lumen having the guide wire placed slideably therein, the guide wire lumen extending in a proximal direction from the tip's distal end, the tip also having a guide wire distal exit port at the tip's distal end through which the guide wire exits from the balloon angioplasty catheter.

2. The balloon angioplasty catheter system of claim 1 wherein the diameter of the distal tip at its proximal end is equal to or larger than the diameter of the uninflated balloon.

3. The balloon angioplasty catheter system of claim 1 wherein the distal tip includes a thin-walled cylindrical section that extends from the proximal end of the distal tip over the blunt distal fold of the uninflated balloon.

4. The balloon angioplasty catheter system of claim 1 wherein the distal tip includes a proximal exit port placed distal to the balloon through which the guide wire can exit from the distal tip thus providing a rapid exchange capability for the balloon angioplasty catheter.

5. The balloon angioplasty catheter system of claim 1 wherein there are two radiopaque marker bands placed coaxially around the shaft of the balloon angioplasty catheter, the two radiopaque marker bands consisting of a proximal radiopaque marker band being located near the proximal end of the balloon and a distal radiopaque marker band being located near the distal end of the balloon.

6. The balloon angioplasty catheter system of claim 1 wherein the average slope angle of the continuous outer surface is less than 3 degrees.

7. The balloon angioplasty catheter system of claim 1 wherein the average slope angle of the continuous outer surface is less than 1.0 degree.

* * * * *